(12) United States Patent
Ha et al.

(10) Patent No.: US 10,669,526 B2
(45) Date of Patent: *Jun. 2, 2020

(54) STEM CELLS DERIVED FROM PURE CHORIONIC TROPHOBLAST LAYER AND CELL THERAPY COMPRISING SAME

(71) Applicant: Samsung Life Public Welfare Foundation, Seoul (KR)

(72) Inventors: Chul Won Ha, Seoul (KR); Jin A. Kim, Gyeonggi-do (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/280,713

(22) Filed: Feb. 20, 2019

(65) Prior Publication Data

US 2019/0177684 A1    Jun. 13, 2019

Related U.S. Application Data

(62) Division of application No. 15/110,654, filed as application No. PCT/KR2015/000204 on Jan. 8, 2015, now abandoned.

(30) Foreign Application Priority Data

Jan. 8, 2014 (KR) ........................ 10-2014-0002308

(51) Int. Cl.
| | | |
|---|---|---|
| *C12N 5/073* | (2010.01) | |
| *A61K 35/50* | (2015.01) | |
| *C12N 5/0775* | (2010.01) | |
| *C12N 5/077* | (2010.01) | |

(52) U.S. Cl.
CPC ............ *C12N 5/0605* (2013.01); *A61K 35/50* (2013.01); *C12N 5/0655* (2013.01); *C12N 5/0668* (2013.01); *C12N 2506/025* (2013.01); *C12N 2506/1392* (2013.01)

(58) Field of Classification Search
None
See application file for complete search history.

(56) References Cited

U.S. PATENT DOCUMENTS

| | | | | |
|---|---|---|---|---|
| 8,057,788 | B2 * | 11/2011 | Hariri ................. | C12N 5/0605 424/93.1 |
| 2006/0211110 | A1 | 9/2006 | Lee et al. | |
| 2007/0134210 | A1 | 6/2007 | Heidaran | |
| 2007/0243172 | A1 | 10/2007 | Ra et al. | |
| 2007/0287176 | A1 | 12/2007 | Rezania | |
| 2016/0324901 | A1 | 11/2016 | Ha et al. | |
| 2016/0326487 | A1 | 11/2016 | Ha et al. | |

FOREIGN PATENT DOCUMENTS

| | | |
|---|---|---|
| KR | 1020070101756 | 10/2007 |
| KR | 10200818214 | 4/2008 |
| KR | 1020080104844 | 12/2008 |
| KR | 1020090076989 | 7/2009 |
| KR | 1020120006386 | 1/2012 |
| KR | 1020130013435 | 2/2013 |
| WO | WO 2008/051568 | 2/2008 |
| WO | WO 2008/146991 | 12/2008 |
| WO | WO 2008/146992 | 12/2008 |
| WO | WO 2012/008733 | 1/2012 |

OTHER PUBLICATIONS

Choi et al., "Different characteristics of mesenchymal stem cells isolated from different layers of full term placenta," PLoS ONE 12(2): e0172642, Feb. 22, 2017.
International Search Report corresponding to International Patent Application No. PCT/KR15/00205, dated Mar. 25, 2015.
International Search Report corresponding to International Patent Application No. PCT/KR15/00204, dated Mar. 24, 2015.
Lee et al., "Comparison of in vitro hepatogenic differentiation potential between various placenta-derived stem cells and other adult stem cells as an alternative source of functional hepatocytes," Differentiation 84(2012) 223-231, Aug. 10, 2012.
Mahooti et al., "PECAM-1 (CD31) expression modulates bleeding time in vivo," Short Communication, American Journal of Pathology 157(1):75-81, Jul. 2000.
Parolini et al., Concise review: Isolation and characterization of cells from human term placenta: Outcome of the first international workshop on placenta derived stem cells., Stem Cell 26(2):300-311, Feb. 2008.
Pipino et al., "Placenta as a reservoir of stem cells: an underutilized resource?," British Medical Bulleting 2013, 105: 43-67, Nov. 25, 2012.
Yeh et al., "Neocartilage formation from mesenchymal stem cells grown in type II collagen-hyaluronan composite scaffolds," Differentiation 86(2013) 171-183, Jan. 24, 2014.
Zhang et al., "Mesenchymal progenitor cells derived from chorionic villi of +human placenta for cartilage tissue engineering," Biochemical and Biophysical Research Communications 340 (2006) 944-952, Dec. 27, 2005.

* cited by examiner

*Primary Examiner* — Nghi V Nguyen

(74) *Attorney, Agent, or Firm* — Leydig, Voit & Mayer, Ltd.

(57) ABSTRACT

The present disclosure relates to stem cells derived from a pure chorionic trophoblast layer (chorionic trophoblast layer without villi, CT-V), which is a part of the tissues of the placenta, and cell therapy comprising same. Stem cells derived from a pure chorionic trophoblast layer according to the present invention exhibit uniform growth characteristic, and superb proliferation and differentiation characteristics compared to the conventional stem cells derived from the whole placenta, and particularly, exhibit excellent differentiation into cartilage cells, thus can be effectively used in cell therapy for treating cartilage damage, deficiency and such, and as a composition for tissue regeneration.

8 Claims, 9 Drawing Sheets

STEM CELLS DERIVED FROM PURE CHORIONIC TROPHOBLAST LAYER AND CELL THERAPY COMPRISING SAME

CROSS-REFERENCE TO RELATED APPLICATIONS

This application is a divisional application of U.S. application Ser. No. 15/110,654, filed Jul. 8, 2016, which is a U.S. National Stage Application under 35 U.S.C. § 371 of International Application No. PCT/KR2015/000204, filed Jan. 8, 2015, which claims the benefit of and priority to Korean Patent Application No. 10-2014-0002308, filed Jan. 8, 2014. Each of these applications is hereby incorporated by reference in its entirety.

TECHNICAL FIELD

The present disclosure relates to stem cells derived from a pure chorionic trophoblast layer (chorionic trophoblast layer without villi, CT-V) which is a part of the tissues of the placenta and a cellular therapeutic agent including the same.

BACKGROUND ART

Recently, biotechnology has proposed the possibility of new solutions to the food, environmental, and health problems as a final goal of human welfare, and among them, a technique using stem cells is emerging as a new technique of incurable disease treatment. For this disease treatment of the human, organ transplantation, gene therapy, and the like have been proposed before, but efficient commercialization is not sufficient due to immune rejection, supplied organs shortage, and lack of knowledge about vector development or disease genes. As a result, an interest in the stem cells is increased, and totipotent stem cells having ability to generate all organs through proliferation and differentiation are recognized to treat most of diseases and essentially solve organ damage. Further, many scientists have variously proposed potential to the stem cells up to treatments of Parkinson's disease which has been incurable, various cancers, diabetes and spinal cord injuries, and the like, as well as regeneration of almost all organs of the human body.

The "stem cells" refer to cells having self-replication capacity as non-differentiated cells and a differentiation capacity into two or more different kinds of cells. The stem cells classified into totipotent stem cells, pluripotent stem cells, and multipotent stem cells according to differentiation capacity, and also may be classified into embryonic stem cells and adult stem cells according to a cytological origin. The embryonic stem cells are derived from an embryo before implantation or a fetus genital tissue during generation; while the adult stem cells are derived from all organs present in the adult, for example, bone marrow, brain, liver, pancreas, and the like.

Since the embryonic stem cells have ethical issue, there is a limitation to be used as a cellular therapeutic agent. On the other hand, the adult stem cells can be mainly extracted from fat, umbilical cord blood, bone marrow, placenta, and the like and have no ethical problem. Particularly, fat stem cell in a fat tissue and placenta stem cells in the placenta during parturition are stable and have excellent differentiation to be used for improving symptoms of various cell damage diseases such as diabetes, dementia, arthritis, myocardial infarction, cerebral infarction, and renal failure which are incurable diseases which are not treated with modern medicine.

Among them, in the case of the stem cells derived from the placenta, by using the placenta discarded after childbirth, it is advantageous that extraction is easy and a large amount of stem cells can be easily ensured. The stem cells derived from the fat or the bone marrow are influenced by ages or health states of donors to be isolated and extracted to have a limitation in proliferation or differentiation capacity and have large variability. However, the ability of the stem cells derived from the placenta are not almost influenced according parameters such as ages of donors as stem cells which may be obtained in the earliest stage among the adult stem cells, and also, such stem cells have excellent proliferation and differentiation abilities. Further, from the stem cells derived from the placenta, a stem cell group which can be used for various diseases such as nervous system disorders, liver diseases, and musculoskeletal diseases may be isolated.

Due to the aforementioned advantages, researches on the stem cells derived from the placenta have been actively conducted. For example, in Korea Patent Registration No. 818214, a method of isolating stem cells from an amniotic membrane or a decidua by using a medium including N-acetyl-L-cysteine (NAC) is proposed, and Korea Patent Registration No. 871984, a method of culturing stem cells derived from an amniotic membrane, a serous membrane, a basal decidua, and a placenta tissue by using a medium including a basic fibroblast growth factor (bFGF) is proposed, and in Korea Patent Publication No. 10-2007-0052204, a method of isolating stem cells from a chorionic villi of a chorionic trophoblast layer of the placenta is proposed. However, until now, researches on stem cells derived from a pure chorionic trophoblast layer which is a part of the tissues of the placenta are not yet conducted.

DISCLOSURE

Technical Problem

Under such circumstances, the present inventors have made intensive studies to develop stem cells having more excellent stem cell capacity from the stem cells derived from the placenta. As a result, present inventors have completed the present disclosure by verifying that the stem cells derived from a pure chorionic trophoblast layer (chorionic trophoblast layer without villi, CT-V) which is a part of the tissues of the placenta exhibit uniform growth characteristic, and superb proliferation and differentiation characteristics as compared with the conventional stem cells derived from the whole placenta, and particularly, exhibit excellent differentiation into cartilage cells, thereby they can be effectively used as a cellular therapeutic agent.

Subsequently, it is an object of this invention to provide stem cells derived from a pure chorionic trophoblast layer which is a part of the tissues of the placenta.

It is another object of this invention to provide a cellular therapeutic agent and a composition for regenerating tissues including stem cells derived from a pure chorionic trophoblast layer which is a part of the tissues of the placenta; or cells differentiated from the stem cells as an active ingredient.

Technical Solution

An aspect of the present disclosure provides stem cells derived from a pure chorionic trophoblast layer which is a part of the tissues of the placenta.

Another aspect of the present disclosure provides a cellular therapeutic agent including stem cells derived from a pure chorionic trophoblast layer which is a part of the tissues of the placenta or cells differentiated from the stem cells as an active ingredient.

Yet another aspect of the present disclosure provides a composition for regenerating tissues including stem cells derived from a pure chorionic trophoblast layer which is a part of the tissues of the placenta or cells differentiated from the stem cells as an active ingredient.

Advantageous Effects

According to the present invention, the stem cells derived from the pure chorionic trophoblast layer (chorionic trophoblast layer without villi, CT-V) can exhibit uniform growth characteristic, and superb proliferation and differentiation characteristics as compared with the stem cells derived from the whole placenta in the related art. Particularly, the stem cells can exhibit excellent differentiation into cartilage cells, thereby they can be usefully used as the cellular therapeutic agent and the tissue regeneration composition for treating cartilage damage, cartilage defect, or the like.

MODES OF THE DISCLOSURE

Hereinafter, the present disclosure will be described in detail.

The present disclosure provides stem cells derived from a pure chorionic trophoblast layer (chorionic trophoblast layer without villi, CT-V) which is a part of the tissues of the placenta.

In the present invention, the "stem cells" refer to cells having self-replication capacity and a differentiation capacity into two or more different kinds of cells. The stem cells may be classified into totipotent stem cells, pluripotent stem cells, and multipotent stem cells according to differentiation capacity.

In the present invention, the "totipotent stem cells" are cells having a totipotent property which can be differentiated into one complete object, the cells up to 8 cell stages after fertilization of the egg and the sperm have the totipotent property, and the totipotent stem cell means the cell to be differentiated into one complete object when the cells are isolated, and then, transplanted into the uterus. In the present invention, the "pluripotent stem cells" are cells which can be differentiated into various cells and tissues derived from ectoderm, mesoderm, and endoderm layers, and are derived from an inner cell mass positioned in the blastocyst shown after 4 to 5 days of the fertilization, which are called embryonic stem cells. The pluripotent stem cells mean cells which are differentiated into various different tissue cells, but do not form a new organism. In the present invention, the "multipotent stem cells" refer to cells which may be differentiated into only specific cells forming a tissue and an organ including stem cells. For the purpose of the present disclosure, the "stem cells" may be preferably the multipotent stem cells.

Figure 1:
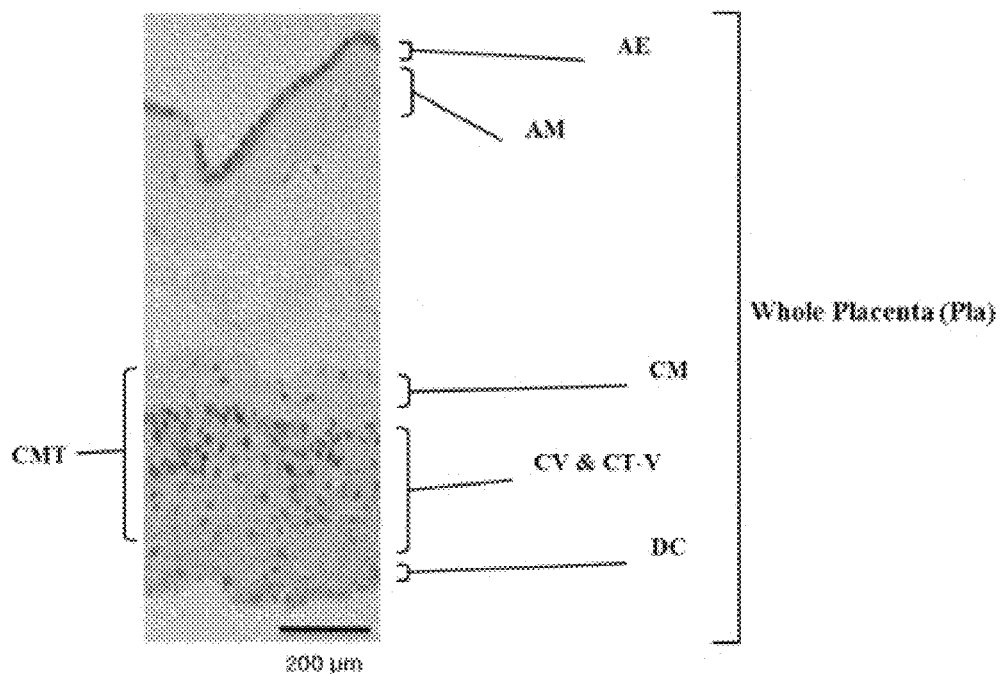
FIG. 1 is a diagram illustrating a form in which amniotic epithelium (AE), an amniotic membrane (AM), a chorionic membrane (CM), a pure chorionic trophoblast layer (chorionic trophoblast layer without villi; CT-V), chorionic villi (CV), and decidua (DC) of the placenta are sequentially laminated from the top, as a micrograph illustrating a cross section of the placenta.

In the present invention, the "placenta" refers to a tissue in vivo made for the fetus during pregnancy and has a disk form having a weight of 500 to 600 g, a diameter of 15 to 20 cm, and a thickness of 2 to 3 cm. One side of the placenta is in contact with the mother and the other side is in contact with the fetus, and nutrients and oxygen are transferred between the blood of the mother and the blood vessel of the fetus between them. The placenta may be largely divided into three layers of the amnion membrane, the chorionic membrane, and the decidua, and more particularly, into the amniotic epithelium, the amnion membrane, the chorionic membrane, the chorionic trophoblast layer, and the decidua. The decidua is a membrane formed when the epithelial cells of the uterine are modified so that the embryos are implanted in the uterus. A cross-sectional view of the placenta is briefly illustrated in FIG. 1.

In the present invention, the "pure chorionic trophoblast layer" refer to a tissue which is removed chorionic villi of the chorionic membrane in the chorionic trophoblast layer positioned between the chorionic membrane and the decidua.

The stem cells derived from the pure chorionic trophoblast layer according to the present invention may be obtained by culturing and then collecting the cells obtained by performing enzyme reaction by adding an enzyme solution to the pure chorionic trophoblast layer tissue isolated from the placenta in a medium added with fetal bovine serum and antibiotics without using growth factors.

More particularly, the stem cells derived from the pure chorionic trophoblast layer according to the present invention may be obtained through the following steps:

(a) isolating a pure chorionic trophoblast layer (chorionic trophoblast layer without villi, CT-V) which is a part of the tissues of the placenta, from the placenta;

(b) obtaining cells derived from the pure chorionic trophoblast layer by treating one or more kinds of enzymes selected from the group consisting of trypsin, collagenase, dispase, DNase, RNase, protease, lipase, hyaluronidase, and elastase in the isolated pure chorionic trophoblast layer tissue; and (c) screening the stem cells from the obtained cells derived from the pure chorionic trophoblast layer.

Hereinafter, a fabrication method of the stem cells derived from the pure chorionic trophoblast layer according to the present invention will be described in detail for each step.

The step (a) is a procedure of isolating the pure chorionic trophoblast layer as a part of the tissues from the placenta, and the isolation method is not particularly limited thereto, but may be performed by a mechanical isolation method using forcep W, a knife, and the like, a chemical isolation method using enzymatic treatment, and the like. Further, after step (a), the blood derived from the placenta may be preferably removed by washing the isolated tissue, and in this case, PBS may be used as a wash solution and is not limited thereto.

The (b) step is a step of obtaining cells derived from the pure chorionic trophoblast layer by treating one or more kinds of enzymes selected from a group consisting of trypsin, collagenase, dispase, DNase, RNase, protease, lipase, hyaluronidase, and elastase in the pure chorionic trophoblast layer tissue. The collagenase includes collagenase A, I, II, III, or IV. As a method of completing the enzyme reaction, a method of adding a medium including the fetal bovine serum may be preferably used, but is not particularly limited thereto.

The step (c) is a step of screening the stem cells from the cells derived from the pure chorionic trophoblast layer, and a screening method may be preferably performed by a method of culturing the cells derived from the pure chorionic trophoblast layer obtained through the step (b) in a culture container, attaching the cultured cells to the bottom of the culture container, and screening the attached cultured cells, but is not limited thereto. In the case, the medium used during the culture may be all media used in the culture of the stem cells, but is not particularly limited thereto. A medium including serum without a growth factor and antibiotics may be preferably used.

According to the present invention, a non-decomposed tissue is removed by filtering the cells obtained in the step (b) with a mesh and the filtered cells are washed using a medium added with the fetal bovine serum and the antibiotics. The washed cells are cultured in a medium added with the fetal bovine serum and the antibiotics without the growth factor and mesenchymal stem cells attached to the bottom of the culture container are screened. The screened mesenchymal stem cells have projected and elongated shapes in appearance to exhibit a similar morphological characteristic to fibroblastic cells.

The stem cells derived from the pure chorionic trophoblast layer as a part of the tissues of the placenta according to the present invention have the following features:

(a) a morphological feature in a fibroblastic cell shape;
(b) a proliferation capacity for a long period so as to reach the passage number of 25 to 30 or more;
(c) a differentiation capacity into adipogenic, chondrogenic, or osteogenic;
(d) a colony formation capacity;
(e) positive immunological characteristics for CD44, CD73, CD90, and CD105; and
(f) negative immunological characteristics for CD31, CD34, CD45, and HLA-DR.

The stem cells derived from the pure chorionic trophoblast layer according to the present invention may be differentiated into different kinds of cells as stated in the following method, and for example, may be differentiated into various kinds of cells such as adipogenic, chondrogenic, osteogenic, neuron, ligament, or tenocyte, and the present disclosure is not limited thereto.

In the present invention, the "differentiation" generally means a phenomenon in which a relatively simple limit is divided into two or more qualitatively different parts and particularly, means a phenomenon in which different structures or functions are specified while the cells are divided, proliferated, and grown, that is, forms or functions are changed so that cells, tissues, and the like of the organism perform given tasks, respectively. On the contrary, the "non-differentiation" means a state in which the aforementioned differentiation does not occur and features as the stem cells are yet included.

A method of differentiating the stem cells may be performed according to an existing known method and is not particularly limited thereto. For example, preferably, the method may be a method of differentiating the stem cells into the adipogenic by culturing the stem cells in a medium including dexamethasone, indomethacin, insulin, and 3-isobutyl-1-methylxanthine (IBMX); a method of differentiating the stem cells into the chondrogenic by culturing the stem cells in a medium including dexamethasone, bone morphogenetic protein 6 (BMP-6), transforming growth factor beta (TGF-β), ascorbic acid, and L-proline; a method of differentiating the stem cells into the osteogenic by culturing the stem cells in a medium including dexamethasone, ascorbic acid, β-glycerophosphate, and ascorbic acid-2-phosphate; and the like.

As a method of measuring the degree of differentiation of the stem cells derived from the pure chorionic trophoblast layer differentiated by the above-described method, a parenchymal cell analysis method, an immunocytochemical method, a method of measuring a cell surface marker or a change in form by using a PCR or a gene-expression profile, a method of examining a morphologic change of the cells by using an optical microscope or a confocal microscope, a method of measuring a change in a gene-expression profile, and the like, which are known in the related art, may be used, but is not limited thereto. Preferably, RT-PCR, an oil-red O staining method, a safranin O staining method, a Type II collagen immunohistochemical staining method, an alkaline phosphate (ALP) staining method, an alizarin red S staining method, or the like may be used.

The stem cells derived from the pure chorionic trophoblast layer (the chorionic trophoblast layer without villi, CT-V) according to the present invention exhibit uniform growth characteristic, and superb proliferation and differentiation characteristics as compared with the stem cells derived from the whole placenta in the related art, and particularly, have excellent differentiation into the chondrogenic.

Accordingly, the present disclosure provides a cellular therapeutic agent including stem cells derived from a pure chorionic trophoblast layer (chorionic trophoblast layer without villi, CT-V) which is a part of the tissues of the placenta or cells differentiated from the stem cells as an active ingredient.

The differentiated cells include adipogenic, chondrogenic, osteogenic, neuron, ligament, tenocyte, and the like and may be selected according to a therapeutic purpose.

The term "cellular therapeutic agent" in the present invention, as a drug (U.S. FDA regulations) used for treating, diagnosing, and preventing by using cells and tissues prepared through isolation from the human, culture, and a specific manipulation, means a drug used for treating, diagnosing, and preventing of diseases by using the cells through a series of actions such as in vitro proliferating and screening living self, homogeneous, or heterogeneous cells for restoring functions of cells or tissues, changing a biological characteristic of the cells by another method, and the like.

Preferably, the cellular therapeutic agent according to the present invention may be used for treating cartilage damage, cartilage defect, bone defect, tendon-ligament defect, or fat tissue defect.

In the present disclosure, the "cartilage defect" has a meaning including damage, defect, or lack of the cartilage included in the body, and for example, includes cartilage injury, cartilage tear, chondromalacia, cartilage necrosis, osteochondritis, cartilage loss, osteoarthritis, or the like, but the present disclosure is not limited thereto.

The stem cells derived from the pure chorionic trophoblast layer according to the present invention may be used in various kinds of treatment protocols which are controlled, reinforced, treated, or replaced by engrafting, transplanting, or infusing a desired cell colony of tissues or organs of the body, for example, a colony of the stem cells or the differentiated cells. The stem cells derived from the pure chorionic trophoblast layer according to the present invention may become a new or changed tissue or be bound with a biological tissue or structure by replacing or reinforcing an existing tissue.

Furthermore, the stem cells derived from the pure chorionic trophoblast layer according to the present invention are transplanted into the joint to treat lesions of the articular cartilage or transplanted into a tendon or ligament portion to be used for treatment or prevention. For example, the stem cells derived from the pure chorionic trophoblast layer according to the present invention are transplanted into the joint, the tendon, or ligament portion to promote the recovery or the adjustment for the damaged portion of the tissue or may be used for reconfiguring or regenerating the tissue of the joint (for example, knee joint and the like) by using a material derived from the stem cells such as a cartilage tissue constructs derived from the stem cells derived from the pure chorionic trophoblast layer of the present disclosure or treating the tissue by methods such as regeneration.

A preferable transplantation amount of the cellular therapeutic agent according to the present invention varies according to a state and a weight of the object, the degree of the disease, a drug form, and transplantation route and period, but may be properly selected by those skilled in the art. The transplantation may be performed once or several times a day, and the transplantation amount does not limit the scope of the present invention even in any way.

Further, the present disclosure provides a composition for regenerating tissues including stem cells derived from a pure chorionic trophoblast layer or cells differentiated from the stem cells as an active ingredient.

The tissues are not particularly limited, but include tissues such as cartilage, fat, bone, nerve, ligament, and tendon, and are preferably cartilage.

The cartilage includes hyaline cartilage, fibrocartilage, elastic cartilage, or the like and for example, may be articular cartilage, ear cartilage, nasal cartilage, elbow cartilage, meniscus, knee cartilage, costal cartilage, ankle cartilage, tracheal cartilage, laryngeal cartilage, or spinal cartilage, but the present disclosure is not limited thereto.

Hereinafter, the present disclosure will be described in more detail with reference to the following Examples. Examples are to describe the present disclosure in detail and the scope of the present disclosure is not limited by Examples.

Example 1: Preparing of Stem Cells Derived from a Pure Chorionic Trophoblast Layer which is a Part of Tissues of Placenta The placenta was collected from the mother agreeing on donation in a normal cesarean delivery at the Samsung Seoul Hospital according to a guideline for clinical test ethics commission of the Samsung Seoul Hospital. The placenta tissue was put in a sterile container and then transferred. After an amniotic membrane was removed from the transferred placenta tissue, a chorionic trophoblast layer positioned between a chorionic membrane (CM) and decidua (DC) was isolated and a pure chorionic trophoblast layer (a chorionic trophoblast layer without villi, CT-V) of the chorionic trophoblast layer was carefully isolated by using sterilized forcep W and knife. A cross-sectional view of the placenta was illustrated in FIG. 1.

The isolated pure chorionic trophoblast layer tissue was washed several times by using PBS to remove blood and blood cells and then finely cut as much as possible. Thereafter, a DMEM medium including 0.2% collagenase was added and reacted with the cut tissue for 2 to 3 hours by using an agitator at 37° C. to obtain cells derived from the pure chorionic trophoblast layer.

The obtained cells derived from the pure chorionic trophoblast layer tissue were filtered with a mesh of 70 μm to remove a non-decomposed tissue and added with a DMEM medium including fetal bovine serum and antibiotics and then centrifuged for 4 min at 25° C. and 1000 rpm. A supernatant was removed, a DMEM medium including fetal bovine serum and antibiotics without a growth factor was added in the remaining precipitated cells, and the cells were cultured under a condition of 37° C. and 5% $CO_2$. The stem cells derived from the pure chorionic trophoblast layer was obtained by screening the cells attached to the bottom of the culture container from the culture.

Comparative Example 1: Preparing of Stem Cells Derived from Whole Placenta

The whole placenta tissue was minced and washed with phosphate buffered saline (PBS) to remove blood and blood cells from the placenta tissue. The washed placenta tissue was added with a DMEM medium including 0.2% collagenase and reacted by using an agitator at 37° C. to obtain placenta cells. The obtained placenta cells were filtered with a mesh of 70 μm to remove a non-degraded tissue and added with a DMEM medium including fetal bovine serum and antibiotics and then centrifuged for 4 min at 25° C. and 1000 rpm. A supernatant was removed, a DMEM medium including fetal bovine serum and antibiotics without a growth factor was added in the remaining precipitated cells, and the cells were cultured under a condition of 37° C. and 5% $CO_2$. The stem cells derived from the whole placenta (Pla) was obtained by screening the cells attached to the bottom of the culture container from the culture.

Example 2: Subculture of Stem Cells Derived from Pure Chorionic Trophoblast Layer which is a Part of Tissues of Placenta The stem cells derived from the pure chorionic trophoblast layer which was a part of the tissues of the placenta obtained in Example 1 were washed with PBS and cultured by replacing a DMEM medium including fetal bovine serum and antibiotics without a growth factor every 2 to 3 days. When the stem cells were grown 80% or more, the stem cells was treated with TryPLE to be isolated from the culture container, and the isolated stem cells were diluted in a ratio of 1/4 and then cultured in another culture container to perform a subculture. While repetitively performing the subculture, the passage number which was not sub-cultured at all was measured, and cell forms before the subculture (P0) and after long-term subculture were observed with a microscope. Further, by using the stem cells derived from the whole placenta (Pla) obtained in Comparative Example 1, the subculture was performed by the same method and then cell forms before the subculture (P0) and after long-term subculture were observed with a microscope. The results are illustrated in FIGS. 2 and 3.

Figure 2:
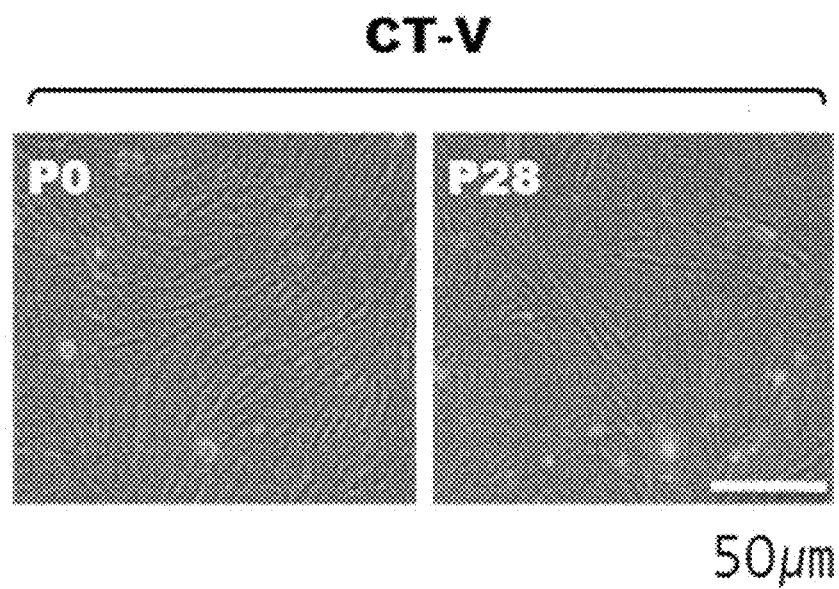
FIG. 2 is a diagram illustrating photographs (×100) which are obtained by observing, by a microscope, cell forms before subculture (P0) and after long-term subculture (P28) of stem cells derived from the pure chorionic trophoblast layer (CT-V) according to the present invention.

As illustrated in FIG. 2, it was verified that the stem cells derived from the pure chorionic trophoblast layer (CT-V) according to the present invention exhibited a fibroblast-shaped morphological characteristic and excellent proliferation capacity until the passage number reached 28, and thus, long-term culture was possible.

Figure 3:
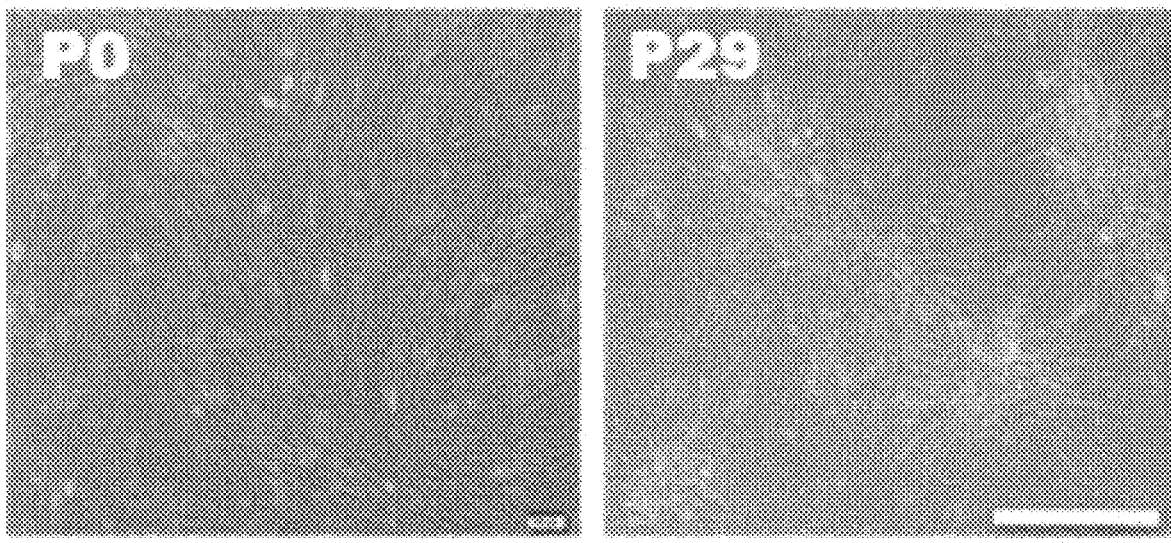
FIG. 3 is a diagram illustrating photographs (×100) which are obtained by observing, by a microscope, cell forms before subculture (P0) and after long-term subculture (P29) of stem cells derived from the whole placenta.

Moreover, as illustrated in FIG. 3, it was verified that the stem cells derived from the whole placenta (Pla) exhibited a fibroblast-shaped morphological characteristic from an early stage of the subculture and a plurality of cells having different shapes other than one shape were mixed. That is, as compared with the stem cells derived from the pure chorionic trophoblast layer (CT-V) according to the present invention (FIG. 2), in the stem cells derived from the pure chorionic trophoblast layer (CT-V) before and after the subculture, only single cells were specifically maintained, but in the stem cells derived from the whole placenta, the cells having different shapes were mixed.

Example 3: Analysis of Colony Formation Capacity of Stem Cells Derived from Pure Chorionic Trophoblast Layer which is a Part of Tissues of Placenta A colony formation capacity of the stem cells derived from the pure chorionic trophoblast layer as a part of the tissues of the placenta obtained in Example 1 was verified. More particularly, in the stem cells derived from the pure chorionic trophoblast layer obtained in Example 1, the first subculture was performed by the method of Example 2, and the stem cells were seeded by $5\times10^3$ in a dish of 100 mm at the time when the subculture was completed and then cultured in a DMEM medium including fetal bovine serum and antibiotics without a growth factor for 10 days. The number of colonies formed in the stem cells was counted by performing a Giemsa staining method in the cultured stem cells and an average value thereof was calculated. Further, by using the stem cells derived from the whole placenta obtained in Comparative Example 1, the colony formation capacity was measured by the same method and the result values thereof were converted to 100%. The results are illustrated in FIG. 4.

Figure 4:
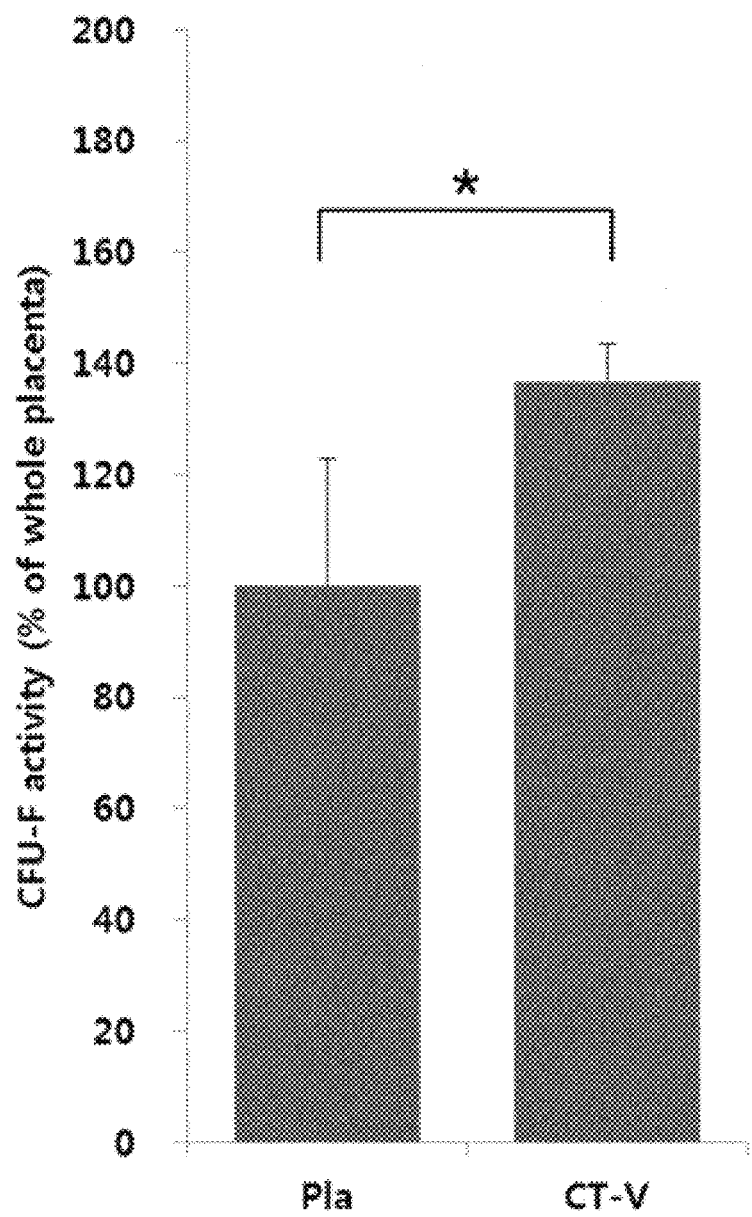
FIG. 4 is a diagram illustrating colony forming units of the stem cells derived from the whole placenta and the stem cells derived from the pure chorionic trophoblast layer (CT-V).

As illustrated in FIG. 4, it was verified that the stem cells derived from the pure chorionic trophoblast layer (CT-V) according to the present invention had the excellent colony formation capacity as compared with the stem cells derived from the whole placenta.

Example 4: Analysis of Population Doubling Time of Stem Cells Derived from Pure Chorionic Trophoblast Layer which is a Part of Tissues of Placenta A population doubling time of the stem cells derived from the pure chorionic trophoblast layer as a part of the tissues of the placenta obtained in Example 1 was measured. More particularly, in the stem cells derived from the pure chorionic trophoblast layer obtained in Example 1, the first subculture was performed by the method of Example 2 and the cells were obtained at an interval of 2 to 3 days and the subculture was repeated. The number of increased cells was verified when the cells were obtained, and $3\times10^5$ cells were cultured on a dish of 100 mm during the subculture. A time when the number of cells was not increased at all during the subculture was defined as a time when the number of cells was not finally increased. The doubling time was measured by the number of cells sub-cultured from P2 to P6 and calculated as follows. Further, using the stem cells derived from the whole placenta obtained in Comparative Example 1, the population doubling time was calculated by the same method. The results are illustrated in FIG. 5.

Doubling time=cultured time/doubling

Doubling=$\log(N_{initial\ cell\ number}/N_{increased\ cell\ number})/\log 2$

Figure 5:
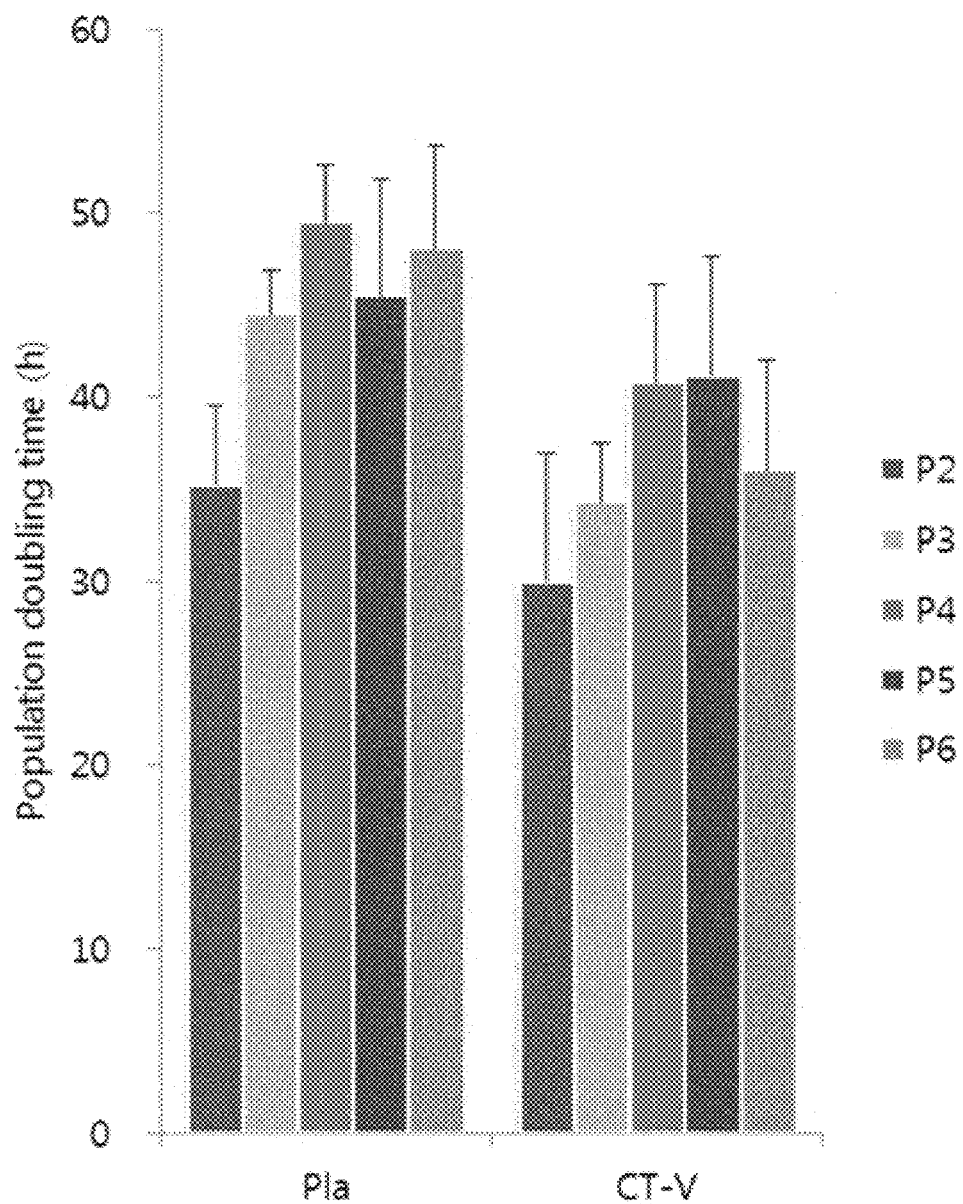
FIG. 5 is a diagram illustrating population doubling times of the stem cells derived from the whole placenta and the stem cells derived from the pure chorionic trophoblast layer (CT-V).

As illustrated in FIG. 5, it was verified that the stem cells derived from the pure chorionic trophoblast layer (CT-V) according to the present invention had a short population doubling time as compared with the stem cells derived from the whole placenta and the cell proliferation was rapid.

Example 5: Analysis of Surface Marker of Stem Cells Derived from Pure Chorionic Trophoblast Layer which is a Part of Tissues of Placenta In order to verify immunological properties of the stem cells derived from the pure chorionic trophoblast layer as a part of the tissues of the placenta obtained in Example 1, the following test was performed. First, the stem cells derived from the pure chorionic trophoblast layer were washed with PBS and treated with TryPLE to collect the stem cells and centrifuged for 4 min at 1000 rpm. The supernatant was removed and a mixed solution of 2% FBS and PBS was added in order to suppress non-specific binding and the stem cells were washed and then centrifuged for 5 min at 1000 rpm. After the supernatant was removed, the stem cells were suspended in the PBS and divided in a flowcytometer-dedicated round flask by $1\times10^5$ cells. A PE-conjugated mouse anti-human monoclonal antibody was added herein, and the stem cells were incubated for 30 min in ice and then centrifuged for 5 min at 1000 rpm. After the supernatant was removed again, the stem cells were washed with the PBS and centrifuged for 5 min at 1000 rpm. The process was repeated two times. Finally, after the supernatant was removed, the stem cells were singled and the immunological properties were analyzed by using a flowcytometer (FACS). Further, immunological properties of the stem cells derived from the whole placenta obtained in Comparative Example 1 were analyzed by the same method. The results are illustrated in Table 1 and FIG. 6.

TABLE 1

|  | CD31 | CD34 | CD45 | CD73 | CD90 | CD105 | HLA-DR | CD44 |
|---|---|---|---|---|---|---|---|---|
| Pla | 0.0% | 0.0% | 0.0% | 97.5% | 98.0% | 100.0% | 0.0% | 92.9% |
| CT-V | 0.0% | 0.0% | 0.0% | 99.1% | 98.0% | 100.0% | 0.0% | 97.0% |

Figure 6:
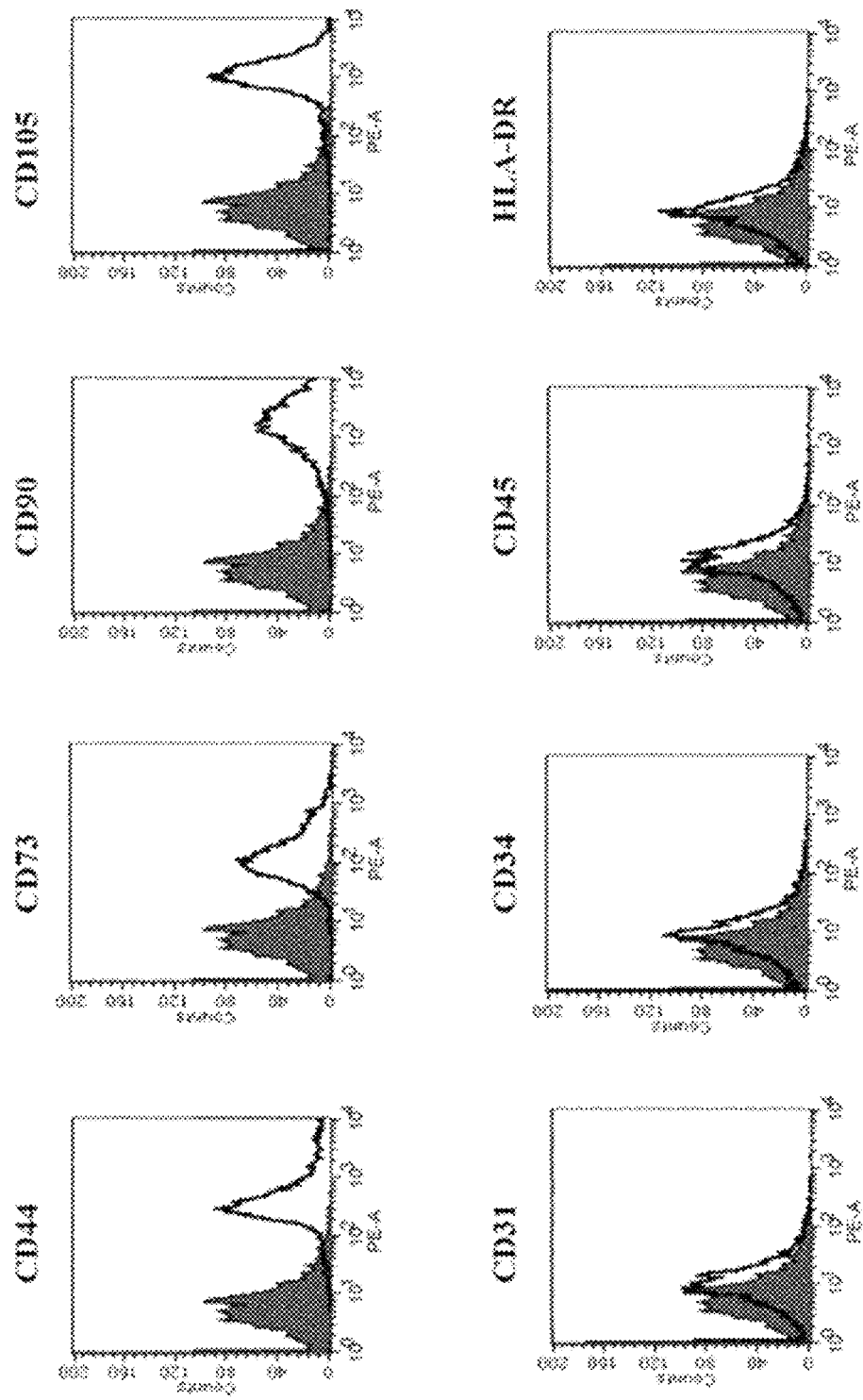
FIG. 6 is a diagram illustrating a parenchymal cell analysis result for verifying a surface factor expression characteristic of the stem cells derived from the pure chorionic trophoblast layer (CT-V) according to the present invention.

As shown in Table 1 and FIG. 6, it was verified that the stem cells derived from the pure chorionic trophoblast layer (CT-V) according to the present invention exhibited positive marker expression characteristics for CD44, CD73, CD90, and CD105 and negative marker expression characteristics for CD31, CD34, CD45, and HLA-DR.

Example 6: Verification of Ability to Differentiate into Chondrocyte of Stem Cells Derived from Pure Chorionic Trophoblast Layer which is a Part of Tissues of Placenta In order to verify differentiation into chondrocyte of the stem cells derived from the pure chorionic trophoblast layer which was a part of the tissues of the placenta obtained in Example 1, the stem cells were cultured for 3 weeks in a known chondrogenic differentiation induced medium (a DMEM medium including 0.1 μM dexamethasone, 50 μg/ml ascorbic acid, 40 μg/ml L-proline, 10 ng/ml TGF-β3, 500 ng/ml BMP-6, and 50 mg/ml ITS premix) to induce the differentiation into the chondrogenic. In order to measure the degree of the differentiation of the stem cells into the chondrogenic, a safranin-O staining method and an immunohistochemical staining method using Type II collagen were performed according to the existing known method. Further, differentiation into the chondrogenic of the stem cells derived from the whole placenta obtained in Comparative Example 1 was measured by the same method. The results were illustrated in FIGS. 7 to 9.

Figure 7:
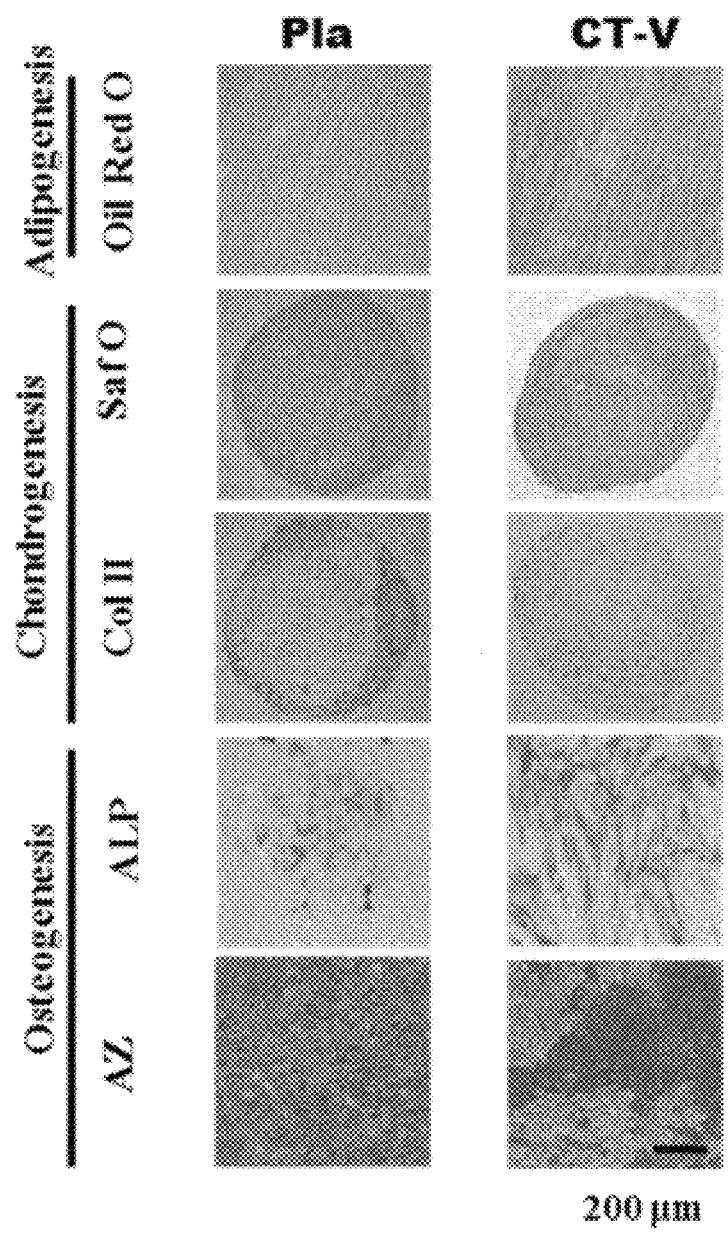
FIG. 7 is a diagram illustrating staining results for observing the degrees of differentiations of the stem cells derived from the whole placenta and the stem cells derived from the pure chorionic trophoblast layer (CT-V) into adipogenic (adipogenesis), chondrogenic (chondrogenesis), or osteogenic (osteogenesis), respectively.
Figure 8:
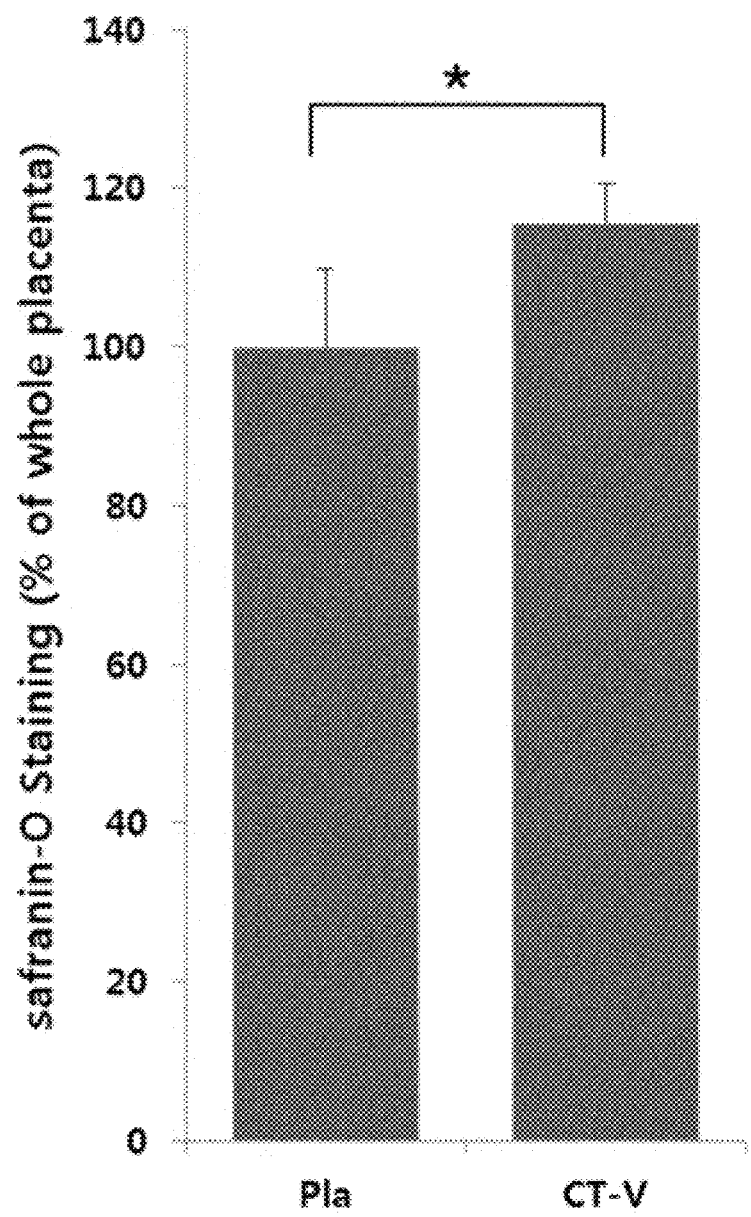
FIG. 8 is a diagram illustrating quantified results obtained after performing staining with Safranin-O for observing the degrees of the differentiations of the stem cells derived from the whole placenta and the stem cells derived from the pure chorionic trophoblast layer (CT-V) into the chondrogenic.
Figure 9:
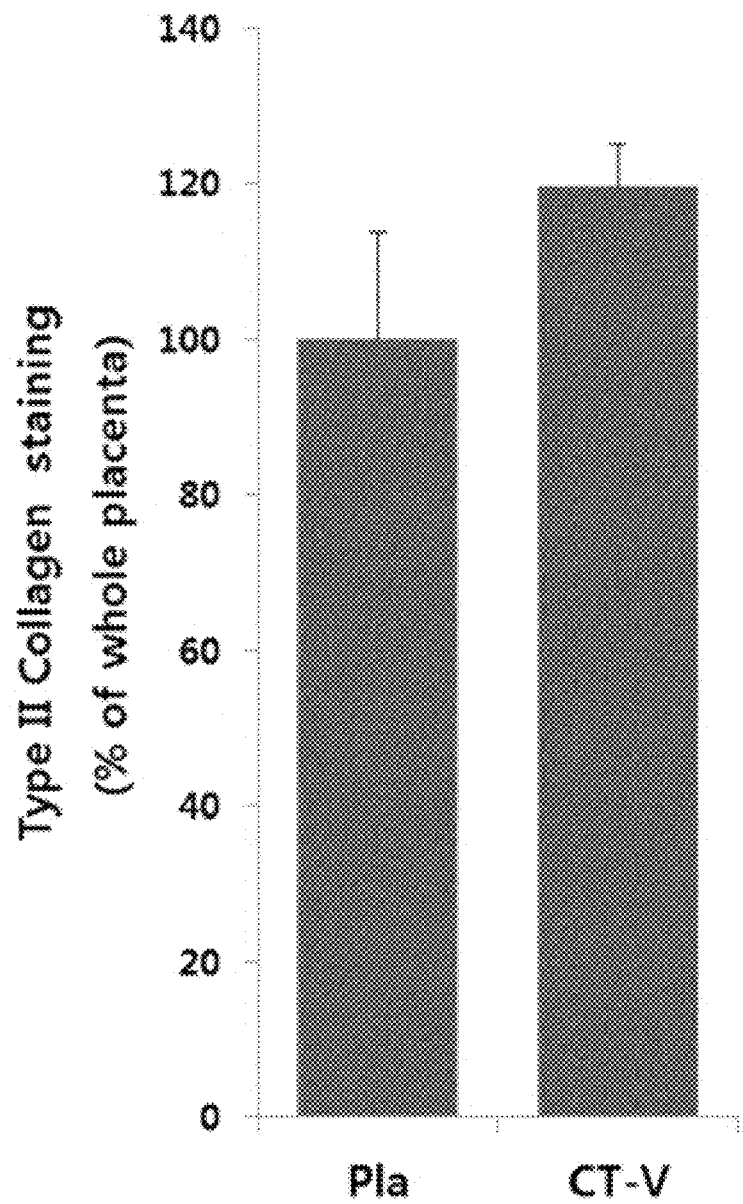
FIG. 9 is a diagram illustrating quantified results obtained after performing immunohistochemical staining using Type II collagen for observing the degrees of the differentiations of the stem cells derived from the whole placenta and the stem cells derived from the pure chorionic trophoblast layer (CT-V) into the chondrogenic.

As illustrated in FIGS. 7 to 9, it was verified that the stem cells derived from the pure chorionic trophoblast layer (CT-V) according to the present invention had the excellent ability of differentiation to the chondrogenic which may be uniformly differentiated into the chondrocyte as compared with the stem cells derived from the whole placenta.

Figure 10:
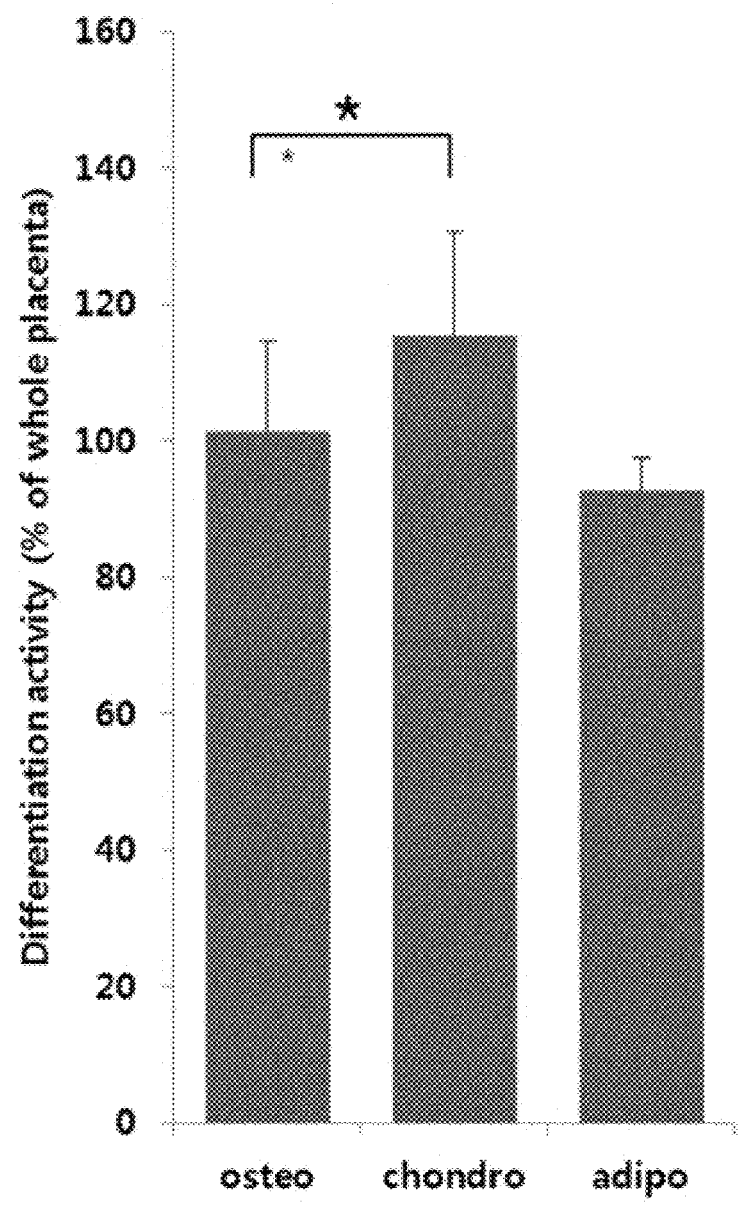
FIG. 10 is a diagram illustrating results of comparing and analyzing the degrees of differentiations of the stem cells derived from the whole placenta and the stem cells derived from the pure chorionic trophoblast layer (CT-V) into adipogenic, chondrogenic, or osteogenic.

Particularly, when comparing and analyzing the activities of differentiations of the stem cells derived from the pure chorionic trophoblast layer and the stem cells derived from the whole placenta into osteogenic, chondrogenic, or adipogenic according to the existing known method, the degrees of the differentiations of the stem cells derived from the pure chorionic trophoblast layer into the adipogenic or the osteogenic were similar to that of the stem cells derived from the whole placenta, but the differentiation into the chondrogenic was particularly excellent (see FIG. 10).

As a result, in the stem cells derived from the whole placenta, the stem cells having different differentiated patterns derived from various tissues are mixed and thus it is slightly insufficient to have a desired cell treatment effect. However, in the case of using the stem cells derived from the pure chorionic trophoblast layer according to the present invention, only the cells having uniform characteristic may be used, the differentiation into the chondrogenic is excellent, and when the stem cells are applied as the cellular therapeutic agent of cartilage damage or diseases requiring cartilage regeneration, the stem cells have an excellent effect.

We claim:
1. A method comprising the steps of:
   (a) isolating a chorionic trophoblast layer which is a part of the tissues of the placenta, from placenta;
   (b) preparing a chorionic trophoblast layer without villi by removing a villi of the chorionic membrane in the chorionic trophoblast layer, thereby providing a pure chorionic trophoblast layer;
   (c) obtaining cells derived from the pure chorionic trophoblast layer by treating one or more kinds of enzymes selected from the group consisting of trypsin, collagenase, dispase, DNase, RNase, protease, lipase, hyaluronidase, and elastase to the prepared pure chorionic trophoblast layer tissue; and
   (d) screening cells from the obtained cells derived from the pure chorionic trophoblast layer to confirm the cells are stem cells derived from a chorionic trophoblast layer without villi which is a part of the tissues of the placenta.

2. The method of claim 1 further comprising the step of transplanting the stem cells to regenerate tissues of a subject in need thereof, wherein the tissue is one or more kinds selected from the group consisting of cartilage, fat, bone, nerve, ligament, and tendon.

3. The method of claim 2, wherein the cartilage is hyaline cartilage, fibrocartilage, or elastic cartilage.

4. The method of claim 2, wherein the cartilage is one or more kinds selected from the group consisting of articular cartilage, ear cartilage, nasal cartilage, elbow cartilage, meniscus, knee cartilage, costal cartilage, ankle cartilage, tracheal cartilage, laryngeal cartilage, and spinal cartilage.

5. The method of claim 1, wherein the screening the cells in step (d) is performed by a method comprising the following steps:
   (i) culturing the obtained cells derived from the chorionic trophoblast layer without villi of the step (c) in a culture container;
   (ii) screening the attached cultured cells wherein the attached cultured cells are attached to the bottom of the culture container.

6. The method of claim 1, further comprising the step of transplanting the stem cells to a subject in need of a cellular therapeutic agent, wherein the stem cells are derived from a chorionic trophoblast layer without villi which is a part of the tissues of the placenta.

7. The method of claim 6, wherein the cellular therapeutic agent is used to treat a subject having cartilage damage, cartilage defect, bone defect, tendon-ligament defect, or fat tissue defect.

8. The method of claim 7, wherein the cartilage defect is selected from the group consisting of cartilage injury, cartilage tear, chondromalacia, cartilage necrosis, osteochondritis, cartilage loss, and osteoarthritis.

\* \* \* \* \*